(12) United States Patent
Wiejak et al.

(10) Patent No.: US 10,973,741 B2
(45) Date of Patent: Apr. 13, 2021

(54) ADHESIVE FOR DENTAL PROSTHESES

(71) Applicant: Cintamani Poland Majewscy i Koć Spólka jawna, Piaseczno (PL)

(72) Inventors: Magdalena Wiejak, Piaseczno (PL); Hanna Tomaszewska, Zalesie Górne (PL); Mateusz Olszewski, Warsaw (PL); Maciej Frydryszak, Piaseczno (PL)

(73) Assignee: CINTAMANI POLAND MAJEWSCY I KOC SPÓLKA JAWNA, Piaseczno (PL)

( * ) Notice: Subject to any disclaimer, the term of this patent is extended or adjusted under 35 U.S.C. 154(b) by 0 days.

(21) Appl. No.: 16/561,745

(22) Filed: Sep. 5, 2019

(65) Prior Publication Data

US 2021/0015715 A1    Jan. 21, 2021

(30) Foreign Application Priority Data

Jul. 18, 2019   (PL) .......................................... 430654

(51) Int. Cl.
    *A61K 6/35*      (2020.01)

(52) U.S. Cl.
    CPC ..................................... *A61K 6/35* (2020.01)

(58) Field of Classification Search
    CPC ........................................................ A61K 6/35
    See application file for complete search history.

(56) References Cited

FOREIGN PATENT DOCUMENTS

| WO | 01/15657 A1 | 3/2001 |
|---|---|---|
| WO | 01/41710 A1 | 6/2001 |
| WO | 02/30317 A1 | 4/2002 |
| WO | 2005/081935 A2 | 9/2005 |

OTHER PUBLICATIONS

Dental Citrosept product packaging materials, Jan. 2017.

*Primary Examiner* — Michael F Pepitone
(74) *Attorney, Agent, or Firm* — Myers Wolin, LLC

(57) ABSTRACT

Adhesive for dental prostheses consists of pharmaceutical glycerin 99.5% in the amount of 29-31 wt %, monopropylene glycol in the amount of 27-29 wt %, purified water in the amount of 22-24 wt %, polyvinylpyrrolidone with a mean molar mass of 360,000 in the amount of 14-16 wt %, carboxymethylcellulose in the amount of 1-3 wt %, dried grapefruit pomace extract in a water-glycerin solvent, containing not less than 1200 mg of naringin per 100 mL of extract in the amount of 0.5-2 wt %, menthol in the amount of 0.05-0.15 wt % and benzalkonium chloride in the amount of 0.01-0.03 wt %.

1 Claim, 1 Drawing Sheet

ADHESIVE FOR DENTAL PROSTHESES

CROSS-REFERENCE TO RELATED APPLICATIONS

This application claims priority under 35 U.S.C. § 119 to PL Application P.430654 filed Jul. 18, 2019, the contents of which are incorporated herein by reference.

FIELD OF THE INVENTION

The subject of the invention is a dental prosthesis adhesive.

BACKGROUND

Dental prostheses are tailored to the individual user, but changes in the gum structure often result in discomfort due to loose or slippery prosthesis. This fact makes it difficult to eat and is embarrassing for users.

Dental prosthesis adhesives are used to temporarily glue dental prostheses to the palate and/or gums, depending on the type of prosthesis. Such adhesives are usually applied to the surface of the prosthesis or mouth at the beginning of the day. Adhesives tend to biodegrade during the day due to the effects of saliva, chewing, aquatic environment and acidic pH.

Intensive work on the development of improved adhesive products for dental prostheses has led to the development of a range of adhesives, both synthetic and natural polymers and resins. These substances are used alone or in combination with various adhesives and other materials to improve adhesion, reduce the flow of adhesive from under the prosthesis, and reduce the amount of dirt and the difficulty of removing adhesive residues from the mouth and prosthesis after use. For example, copolymers of alkylvinyl ether-maleic acid are known to provide good adhesion to dental prostheses in adhesive compositions, which is known from publications WO 01/15657 A, WO 02/30317 A, WO 01/41710 A, WO 05/081935 A, and many others.

In addition to adhesion, it is desirable to limit outflow or the negative aesthetic properties of outflow for the consumer. Outflow may occur because of leakage of dental adhesives from under the dental plate in the mouth caused by a number of factors, including low-viscosity adhesives for dental prostheses, using an excessive amount of dental adhesives, improper application of dental adhesives on dental prostheses, etc. Adhesive compositions for dental prostheses are used in the oral cavity for 6-7 hours or longer. In addition, consumers may stop using adhesive or tend to use less adhesive the next time they experience an unpleasant outflow-related sensation. This can lead to reduced adhesion of the prosthesis or worse performance of the prosthesis. This deterioration in performance can mean less stability in the dental prosthesis, as well as accumulation of food under the dental prosthesis.

High force causing the prosthesis to detach from the substrate should be an important and desired feature of the adhesive. However, this force should be properly balanced, so that the prosthesis can be detached only when the force exceeds the forces occurring during normal use, and at the same time not excessively high, allowing the prosthesis to be removed at any time it is needed.

Another feature of the adhesive should be the possibility of multiple application and removal using a single adhesive portion. It is desirable to rinse the prosthesis between subsequent placements without any additional dose of adhesive, so the adhesive cannot dissolve too quickly in water, and at the same time it should be easily washable at the end of use, e.g. before the next application of adhesive, or overnight.

A preparation for oral care called Citrosept Dental in the form of gel with antibacterial properties is known. The product has the form of an adhesive gel which soothes irritated mucous membranes. The product has clinically proven efficacy in the prevention of fungal infections of the oral cavity in persons using prostheses. The preparation has the following composition:

pharmaceutical glycerine 99.5%—30 g/100 g
propylene glycol—30 g/100 g
Kollidon 90K (polyvinylpyrrolidone with a molar weight of 100 000-150 000)—15 g/100 g
grapefruit extract—1 g/100 g
menthol—0.1 g/100 g
benzalkonium chloride—0.01 g/100 g
water—23.89 g/100 g An extract of dried grapefruit pomace in a water-glycerin solvent containing not less than 1200 mg of naringin per 100 mL of extract is used.

Citrosept Dental is not offered as a prosthesis adhesive, but as a soothing agent for irritated mucous membranes. This preparation has some adhesive properties, but its purpose is completely different. According to the leaflet: after brushing teeth apply a small amount of gel on gums and/or palate, do not rinse, do not eat or drink for 1 hour. Use 3-4 times a day.

Known adhesives or gels show either insufficient detachment strength, or the detachment time is too short, or the adhesives have an unpleasant taste, or it is difficult to remove them from the prosthesis, or they retain the ability to adhere again only a few times or even they do not retain it at all without applying another dose of adhesive, or they show several defects at the same time in terms of certain properties.

An extremely important aspect is the development of an adhesive that can be applied in larger quantities to the prosthesis, which will significantly increase the force needed to break the prosthesis off. The previously known adhesives are applied in small quantities in spots. The reason for this application is the attribute of known adhesives, namely that the strong holding of a prosthesis simultaneously results in too much force needed for its removal. In addition, known adhesives are difficult to wash away from the prosthesis, and other adhesives are not suitable for re-application without another dose of adhesive. Thus, on the one hand the application of more adhesive is desirable, and on the other hand, it results in a number of disadvantages, described above. So far, it has not been possible to develop an adhesive which, when applied in large quantities, at the same time would not acquire any undesirable properties.

There is a need to develop an adhesive that will be free of most of the foregoing disadvantages, and preferably all the disadvantages, in a single product.

DETAILED DESCRIPTION

Figure 1:
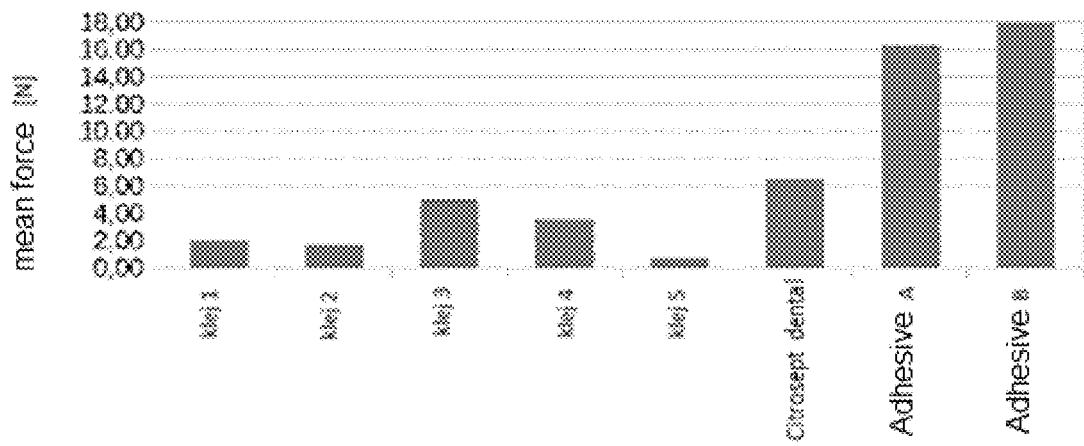
FIG. 1 illustrates the averaged measured force at immediate detachment.

According to the invention, the adhesive consists of 99.5% pharmaceutical glycerin in the amount of 29-31 wt %, monopropylene glycol in the amount of 27-29 wt %, purified water in the amount of 22-24 wt %, polyvinylpyrrolidone with a mean molar mass of 360,000 (PVP K360) in the amount of 14-16 wt %, carboxymethyl cellulose in the amount of 1-3 wt %, dried grapefruit pomace extract in the amount of 0.5-2 wt %, menthol in the amount of 0.05-0.15 wt %, and benzalkonium chloride in the amount of 0.01-0.03 wt %. Dried grapefruit pomace extract in a water-glycerol solvent is used as a grapefruit extract, containing not less than 1200 mg of naringin per 100 mL of the extract.

According to the invention, the adhesive eliminates all use-related inconveniences of known market adhesives.

According to the invention, the adhesive differs from the prior art adhesives and the Citrosept Dental preparation, not used for bonding prostheses, by using a polyvinylpyrrolidone thickener with an average molar mass of 360,000 (PVP K360) in the amount of 14-16 wt %, and simultaneously carboxymethyl cellulose in the amount of 1-3 wt %. In the case of known adhesives, if they use two thickening substances simultaneously, it is carboxymethyl cellulose in combination with cellulose gum. As shown in the examples, the parameters of the adhesive according to the invention confirm that the combined use of polyvinylpyrrolidone with a mean molar mass of 360,000 (PVP K360) in the amount of 14-16 wt %, and at the same time the carboxymethyl cellulose in the amount of 1-3 wt %, unprecedented in this type of product, allowed the use of the adhesive in much larger quantities, but without any of the previously occurring disadvantages.

In addition, according to the invention, apart from effectively bonding the dental prosthesis, the adhesive has the function of a gel dressing for mucous membranes. According to the conducted research, 27% of prosthesis users experience the problem of fungal infections in the oral cavity, and in about 10% it is a recurring problem. Most patients suffering from oral mycosis must give up wearing the prosthesis for the treatment period, and one of the important recommendations for such problems is to replace the prosthesis, which is a fungal reservoir due to its porosity. According to the invention, the adhesive, as the only one, can be used simultaneously for bonding and preventing superinfection, and eliminates the need to replace the prosthesis after treatment, as it creates a mechanical barrier against fungi residing in the dental prosthesis. Additionally, it promotes the healing of mechanical injuries of mucous membranes in the oral cavity, which occur in 45% of prosthesis users.

EXAMPLE

Description of the Performance of the Bonding Test
Equipment:
  dynamometer
  dental prosthesis
  palate model
  beaker
  string
  rack
Test Method:
  Six products available on the market and two adhesives according to the invention were applied on the surface of the prosthesis. Application according to the instructions on the packaging in the case of products available on the market, or our own procedures in the case of new formulations according to the invention.
  Next, the prosthesis was attached to the palate model. A series of measurements characterizing the appropriate adhesive was made using a dynamometer. The same experimental conditions were used, and the mass and adhesive application method, clamping force and adhesion time were taken into account.

Each prepared adhesive was subjected to several tests. The first was the immediate separation of the dental prosthesis from the palate model. A dynamometers was used to measure the force needed to detach the prosthesis from the palate model attached with a given adhesive. The experiment was repeated several times. Each time, the prosthesis and palate model was washed and dried, and new adhesive was applied. The obtained results were recorded.

The next test was the measurement of the time the prosthesis was held to the palate at a constant force of 2N, maintained with a dynamometer attached to the tensioned string and the rack. Every force and time was recorded. The test was repeated several times after the application of a new amount of adhesive.

Then, using the remaining adhesive on the prosthesis, the prosthesis was bonded to the palate model again and the holding force was measured. It was bonded until the prosthesis did not adhere. The number of attachments preceding the test and the attachment force were recorded.

A prosthesis in the oral cavity is exposed to difficult conditions, including a temperature of about 35° C., permanently or temporarily higher, the presence of water, and low pH. In such conditions, the prosthesis should remain for 8-10 hours in the oral cavity. Therefore, the attachment force of the prosthesis was measured after a water bath lasting 5, 10, and 15 minutes, and 12 hours, and after a water bath at a reduced pH.

Cleaning is an important part of using a dental prosthesis. Washing the dental prosthesis consisted in gentle cleaning under running water at room temperature, under running hot water, and brushing with a toothbrush. Subjective sensations related to washing were recorded.

The following products were tested:

TABLE 1

| Designation of the tested product | Composition of the tested product |
|---|---|
| Known market products | (qualitative composition, quantitative composition is not known) |
| Adhesive 1 | Mixture of Na and Ca salts of methylvinyl ether copolymer, W-180 petrolatum, sodium carboxymethyl cellulose, mineral oil, spray-dried peppermint, spray-dried green mint, erythrosine paste, propylparaben. |
| Adhesive 2 | Mixture of Na and Ca salts of a methylvinyl ether and maleic anhydride copolymer, carboxymethyl cellulose, paraffin, petrolatum, colloidal silicon dioxide. |
| Adhesive 3 | Calcium-zinc PVM/MA copolymer, mineral oil, cellulose gum, petrolatum, silicon dioxide, colorant, flavor, menthol. |
| Adhesive 4 | Cellulose gum, calcium-zinc PVM/MA copolymer, mineral oil, petrolatum, chamomile |

TABLE 1-continued

| Designation of the tested product Known market products | Composition of the tested product (qualitative composition, quantitative composition is not known) |
|---|---|
| Adhesive 5 | Mineral oil, calcium-zinc PCM/MA copolymer, cellulose gum, petrolatum, water, polyethylene, peppermint, menthol, colorant, flavor. |
| Market preparation Citrosept Dental oral hygiene gel Comparative test | pharmaceutical glycerin 99.5%-30 wt %, propylene glycol 30 wt %, Kollidon 90K (polyvinylpyrrolidone with a molar mass of 100,000-150,000) 15 wt %, grapefruit extract 1 wt %, menthol 0.1 wt %, benzalkonium chloride 0.01 wt. %, water 23.89 wt % An extract of dried grapefruit pomace in a water-glycerin solvent containing not less than 1200 mg of naringin per 100 mL of extract is used. |
| Adhesive A according to the invention | pharmaceutical glycerin 30 wt %, monopropylene glycol 28.75 wt %, purified water 23.85 wt %, polyvinylpyrrolidone with a mean molar mass of 360,000 (PVP K360) 15.00 wt %, carboxymethylcellulose 1.25 wt %, grapefruit extract 1.00 wt %, menthol 0.13 wt %, benzalkonium chloride 0.02 wt %. An extract of dried grapefruit pomace in a water-glycerin solvent containing not less than 1200 mg of naringin per 100 mL of extract is used. |
| Adhesive B according to the invention | pharmaceutical glycerin 30 wt %, monopropylene glycol 27.50 wt %, purified water 23.88 wt %, polyvinylpyrrolidone with a mean molar mass of 360,000 (PVP K360) 15.00 wt %, carboxymethylcellulose 2.50 wt %, grapefruit extract 1.00 wt %, menthol 0.10 wt %, benzalkonium chloride 0.02 wt % An extract of dried grapefruit pomace in a water-glycerin solvent containing not less than 1200 mg of naringin per 100 mL of extract is used. |

TABLE 2

Comparison of the measured force at immediate detachment (see FIG. 1 for averaged measured force at immediate detachment):

| Product Name | Measured force at immediate detachment [N] | | | | | | Mean force [N] |
|---|---|---|---|---|---|---|---|
| Adhesive 1 | 0.25 | 0.34 | 0.93 | 3.11 | 3.55 | 4.01 | 2.03 |
| Adhesive 2 | 0.26 | 0.4 | 1.23 | 2.04 | 2.25 | 3.91 | 1.68 |
| Adhesive 3 | 3.85 | 4.05 | 4.96 | 5.46 | 5.51 | 5.82 | 4.94 |
| Adhesive 4 | 2.19 | 2.49 | 2.68 | 3.72 | 4.96 | 5.04 | 3.51 |
| Adhesive 5 | 0.41 | 0.55 | 0.61 | 0.77 | 0.99 | 1.16 | 0.75 |
| Citrosept Dental | 1.53 | 1.79 | 5.01 | 6.4 | 10.77 | 13.39 | 6.48 |
| Adhesive according to invention A | 16.44 | 14.58 | 16.63 | 15.28 | 17.44 | 17.07 | 16.24 |
| Adhesive according to invention B | 18.39 | 15.95 | 23.42 | 15.83 | 17.59 | 16.32 | 17.92 |

TABLE 3

Comparison of the measured prosthesis detachment time at 2 N force applied

| Product Name | Measured prosthesis detachment time at 2 N force applied [s] | | | | | Mean time [s] |
|---|---|---|---|---|---|---|
| Market Adhesive 1 | 0.68 | 1.25 | 1.51 | 2.83 | 4.12 | 2.08 |
| Market adhesive 2 | 0.14 | 0.61 | 0.72 | 0.99 | 1.01 | 0.69 |
| Market Adhesive 3 | 2.31 | 4.28 | 6.37 | 11.63 | 17.64 | 8.45 |
| Market Adhesive 4 | 1.90 | 5.84 | 3.87 | 5.99 | 35.76 | 10.67 |
| Market Adhesive 5 | 0.30 | 0.40 | 0.60 | 0.70 | 0.90 | 0.58 |
| Citrosept Dental | 10.14 | 19.16 | 52.75 | 80.18 | 30.52 | 38.55 |
| Adhesive according to invention A | 57.10 | 89.70 | 16.10 | 97.40 | 23.70 | 56.80 |
| Adhesive according to invention B | 23.20 | 42.40 | 85.20 | 72.50 | 122.30 | 69.12 |

TABLE 4

Figure 2:
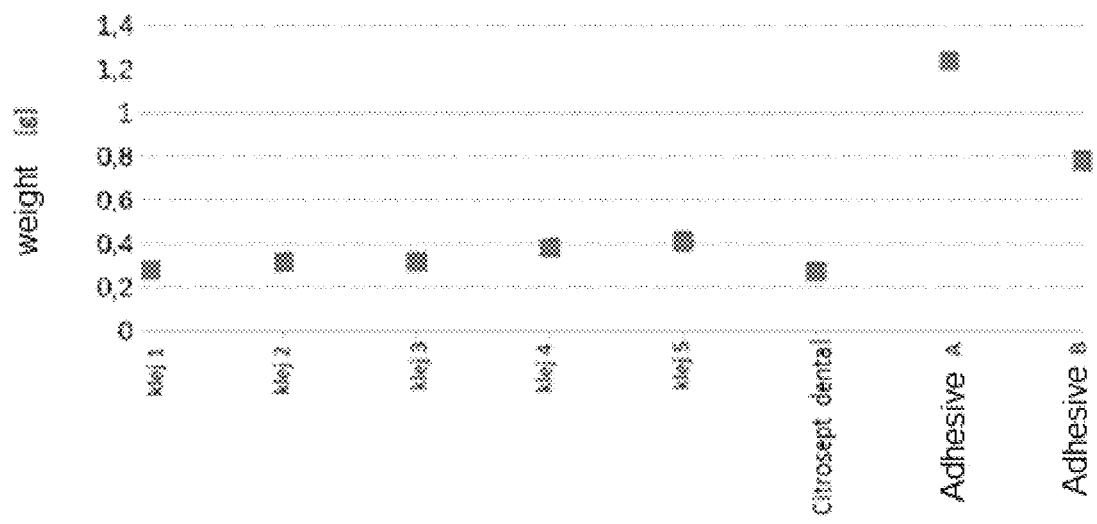
FIG. 2 illustrates the mean weight of applied product [g].

Comparison of mean applied product weight (see FIG. 2 for Mean weight of applied product [g]):

| Product Name | Mean weight of applied product [g] |
| --- | --- |
| Adhesive 1 | 0.28 |
| Adhesive 2 | 0.32 |
| Adhesive 3 | 0.32 |
| Adhesive 4 | 0.38 |
| Adhesive 5 | 0.41 |
| Citrosept Dental | 0.27 |
| Adhesive A | 1.24 |
| Adhesive B | 0.78 |

Adhesive 1

The mean weight of the applied cream is 0.28 g. The method of applying the cream to the prosthesis recommended by the manufacturer is 3 application spots on the prosthesis. The mean attachment force measured at immediate detachment is 2.03N. The mean holding time of a prosthesis with 2N applied is 2.08 s. The prosthesis can be re-applied four times without a new layer of product. Each re-application reduces the prosthesis holding time. Dental prosthesis cream lasts longer when the surface of the prosthesis is moistened with water first. The cream clearly swells and fills the depressions in the prosthesis, causing the prosthesis to adhere more closely to the palate. An acidic pH does not affect the holding power of the prosthesis to the palate model. The cream does not withstand the prosthesis holding test after incubation for 12 hours at 35° C. The more product applied, the stronger and longer the prosthesis hold. Washing under lukewarm running water takes a long time; washing with a toothbrush is more effective. The taste of the cream is indistinct; the mint is unnoticeable.

Adhesive 2

The mean weight of the applied cream is greater than that of Adhesive 1, despite the same application method, i.e. three spots on the prosthesis, and it is 0.32 g. The mean force measured at detachment is 1.68 N. The prosthesis can only be reattached twice to the palate model with the same cream. The prosthesis breaks away immediately at a constant force of 2N. The presence of water, incubation at 35° C. and acidic pH makes it easier for the prosthesis to detach from the palate model. Washing under running water is difficult; the cream enters the cavities on the prosthesis. With the help of a toothbrush, adhesive residues are easily removed from the prosthesis. The taste of the cream is similar to that of Adhesive 1.

Adhesive 3

The average mass of adhesive applied is the same as for Adhesive 2 and is 0.32 g. The mean measured force at immediate detachment is 4.94N and the mean detachment time at approx. 2N is 8 seconds. If the prosthesis is wetted during the adhesive application, the test results are even better. The prosthesis can be reattached four more times without losing the force at the immediate detachment. After a water bath lasting 12 hours at 35° C., the force with which it is possible to detach the prosthesis is about 4N. Cleaning with a toothbrush is easy, and it is quite long, yet possible, under water alone. The taste of the mint is slightly noticeable.

Adhesive 4

The weight needed to obtain the prosthesis adhesion to the palate is higher than in previous products and amounts to approx. 0.38 g. The mean measured force at immediate detachment is 3.51N. The detachment time at a force of about 2N is not repeatable, and the mean is 10 seconds. The prosthesis can be reattached three times without losing the force of the immediate detachment. The product loses its adhesive properties after a water bath. The weight of the cream applied to the prosthesis changes the strength of the attachment. The more it is applied, the better it holds the prosthesis to the palate. It is very difficult to remove the cream from the prosthesis. After removal, it leaves a slippery layer on the toothbrush and prosthesis.

Adhesive 5

In order to achieve the right adhesive strength it is necessary to apply much more cream than in the case of other products. The mean weight is 0.41 g. The measured force at immediate detachment is 0.75N. With a force of approx. 2N the prosthesis detachment from the palate model is immediate. The prosthesis can be reattached only once without losing the strength of the immediate detachment. Water causes immediate cream breakdown. After tests with this product, the prosthesis is hard to clean. A slippery residue remains, which is removed after long soaking in warm water.

Citrosept Dental

The gel is applied to the entire prosthesis, unlike previous products. The mean mass of applied gel is 0.27 g. The measured force at immediate detachment is 6.48 N. With applied force of approx. 2N, the detachment of the prosthesis from the palate model is the longest of all products, taking 38 seconds. The prosthesis can be reattached six times without loss of immediate detachment force. Water causes gradual dissolution of the gel and slow detachment of the prosthesis from the palate. Testing after a water bath causes the prosthesis to detach from the palate model immediately. The prosthesis can be easily washed, even under lukewarm running water. The gel is distinguished by its taste compared to all other tested products. The delicate taste of mint is noticeable. There is no sensation of a residue being left on the palate and the tongue.

Adhesive A

The adhesive is applied to the entire dental prosthesis. The mean mass of the adhesive applied is much higher than the mass of the other tested products, and amounts to 1.24 g. The force measured during immediate detachment is 16.24N. It is quite difficult to detach the prosthesis with an applied force of about 2N, taking a mean time of 56 seconds. The prosthesis can be reattached six times. Water, similarly to Adhesive 6, causes gradual dissolution of adhesive, but a water bath for 5, 10 and 15 minutes does not cause immediate detachment of the prosthesis. The bonded prosthesis does not withstand a 12-hour bath. The adhesive can be washed away under running warm water, but more time is needed than with Adhesive 6. The taste is similar to Adhesive 6, very refreshing.

Adhesive B

The adhesive is applied to the entire surface of the prosthesis. The mean weight of the adhesive is higher than that of the competitor products tested, but lower than that of the previous formulation, and amounts to 0.78 g. The mean measured force during immediate detachment is 17.92N, and the mean detachment time at 2N is 69 s. The prosthesis can be reattached six times. Water dissolves the adhesive, but a 12 h water bath does not cause loss of adhesive properties. The adhesive can be washed away under running warm water. The taste is refreshing; the mint is noticeable.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. Adhesive for dental prostheses, consisting of pharmaceutical glycerin 99.5% in the amount of 29-31 wt %, monopropylene glycol in the amount of 27-29 wt %, purified water in the amount of 22-24 wt %, polyvinylpyrolidone with a mean molar mass of 360,000 in the amount of 14-16 wt % and carbroxymethylcellulose in the amount of 1-3 wt % as thickeners, dried grapefruit pomace extract in a water-glycerol solvent containing not less than 1200 mg of naringin per 100 mL of the extract in the amount of 0.5-2 wt %, menthol in the amount of 0.05-0.15 wt %, and benzalkonium chloride in the amount of 0.01-0.03 wt %.

* * * * *